United States Patent [19]

Brandt et al.

[11] 4,299,814

[45] Nov. 10, 1981

[54] RADIOIMMUNOASSAY OF MIF

[75] Inventors: Eva J. Brandt, Ellisville; Samuel S. Asculai, St. Louis, both of Mo.

[73] Assignee: Monsanto Company, St. Louis, Mo.

[21] Appl. No.: 42,662

[22] Filed: May 25, 1979

[51] Int. Cl.³ .................. G01N 23/48; G01T 1/00
[52] U.S. Cl. ................................ 424/1; 23/230 B; 424/12
[58] Field of Search .................. 424/1, 12; 23/230 B

[56] References Cited

PUBLICATIONS

Rocklin, J. Immunol., 112, 1461–1466 (1974).
Fox et al., Immunol. Communications, 3, 375–389 (1974).
McLeod et al., Cell. Immunol., 32, 370–384 (1977).
David, Fed. Proc., 30(6), 1730–1735 (1971).

*Primary Examiner*—Benjamin R. Padgett
*Assistant Examiner*—Christine M. Nucker
*Attorney, Agent, or Firm*—Scott J. Meyer; James W. Williams, Jr.

[57] ABSTRACT

A method is disclosed for detecting the presence of migration inhibitory factor (MIF) which comprises reacting a test solution containing an unknown amount of MIF antigen, a known amount of MIF antigen which has been radiolabeled, a known amount of antibodies to MIF, and thereafter precipitating and removing the resulting immune complex and measuring the radioactive content thereof, said antibodies to MIF being produced by immunization of animals with MIF antigen obtained from the growth of human lymphocytes under tissue culture conditions.

1 Claim, 1 Drawing Figure

RADIOIMMUNOASSAY OF MIF

BACKGROUND OF THE INVENTION

This invention relates to the radioimmunoassay of migration inhibitory factor and related mediators produced by human lymphocytes.

Migration inhibitory factor (MIF) is a macromolecular product that inhibits macrophage migration. The biochemical nature of MIF produced by sensitized lymphocytes has been elucidated by David, *Proc. Nat. Acad. Sci. U.S.* 56, 72–77 (1966); *Fed. Proceedings* 30, 1730–35 (1971); and by Rocklin, *J. Immunol.* 112, 1461–66 (1974).

Sensitized lymphocytes are believed to play an important role in a number of biological reactions including delayed hypersensitivity, resistance to certain microorganisms and tumors, rejection of transplant tissues and even autoimmune diseases. These sensitized lymphocytes, when stimulated by antigens or mitogens, synthesize and secrete MIF and other soluble mediators.

Since MIF and MIF-like substances are believed to play an important role as mediators of cellular immunity, their evaluation or quantitation is of considerable interest. Various techniques currently are available for evaluating these mediators produced by lymphocytes. The methods are all complicated in vitro bioassay procedures which involve measuring the areas of cell migration in the presence and absence of the mediators. [See Clausen, *Acta Allergol.* 26, 56–80 (1971); id. at 28, 145–58 and 351–64 (1973)]. Consequently, they are unsuitable for routine hospital or clinical laboratory use and generally are performed only in basic and applied research laboratories. A non-bioassay method for the determination of MIF and MIF-like mediators would have significant advantages over the current bioassay methods insofar as it would be less cumbersome for clinical laboratory use and would be more quantitative.

BRIEF DESCRIPTION OF THE INVENTION

In accordance with the present invention a radioimmunoassay (RIA) has been developed for the determination of MIF and MIF-like mediators produced by human lymphocytes.

An important and practical advantage of RIA is that this general type of test for the quantitation of hormones and other antigens (or antibodies) in very low levels has been available in hospital and clinical laboratories for more than a decade. Physicians and medical technologists are familiar with the general principles of RIA and are thus more readily adaptable to acceptance of RIA tests than the more cumbersome and complicated bioassays.

In the general diagnostic procedures involving RIA, unlabeled antigen is measured by its effect on the binding of a predetermined amount of specific antibody to radiolabeled antigen. These RIA procedures depend on the production, purification and radiolabeling of antigen, the induction of antibodies with a high specificity and affinity for the antigen, and a technique for separation of antibody-bound and unbound antigen. General methods for carrying out RIA are well-known and a number of reviews on the subject are available which consider the general principles involved in RIA. Two such reviews with many useful references appended thereto are those of Skelley et al., *Clin. Chem.* 19 (2), 146–186 (1973) and Butler, *J. Immunological Methods* 7, 1–24 (1975).

Notwithstanding the present status of the field of RIA, RIA tests for MIF and MIF-like mediators of cell immunity have not been developed heretofore, although the possibility of such a test has been suggested by McLeod et al., *Cell. Immunol.* 32, 370–84, at 383 (1977). A number of difficult technical problems had to be overcome by the present inventors in order to develop the herein disclosed RIA test for these mediators.

Initially, it was found desirable to develop a continuous culture, transformed human lymphocyte cell line to produce the MIF antigen. For human diagnostic test development purposes, use of continuous culture lymphocytes offers advantages over antigen or mitogen stimulated normal human cells or animal lymphocytes such as obtained from guinea pig and the like animal species. Continuously cultured human lymphocytes provide a reliable source for the reproducible production of human lymphokines in quantities adequate for purification procedures.

It was then determined to be advantageous to grow these human lymphoid cells under suspension culture conditions to provide a reliable, large volume source of MIF antigen.

Another difficult aspect of this development was the purification of MIF antigen to permit the induction of antibodies against MIF, that is, antibodies having a high specificity to MIF antigen. Purification of the MIF antigen by affinity chromatography with fucosamine-agarose resin is advantageous.

Following the development of a partially purified MIF antigen, the antibodies against this antigen are produced in a manner generally similar to known methods for producing antibodies such as by immunizing a suitable animal host, for example, rabbits, guinea pigs and the like animals, by repeated injections of small amounts of the MIF antigen combined with an adjuvant such as, for example, Freund's complete adjuvant. The antibodies produced in the animal are then recovered from the blood serum of the animal after a suitable immunization period. The presence of antibodies in the sera is determined by standard immunologic techniques of double diffusion gel precipitation in agar gel, electrophoresis and immunoelectrophoresis.

Radiolabeling of the MIF antigen also is carried out essentially by standard methods known in the art. The radiolabeling method of Hunter and Greenwood using $^{125}$Iodine is particularly useful. [See *Biochem. J.* 89, 114 (1963) and 91, 46 (1964)]. Other isotopes such as, for example, $^{131}$I, $^{14}$C and $^3$H, also can be used but are less preferred than the $^{125}$I.

The RIA of MIF is then carried out by the competitive-inhibition method in which an antibody titration curve and then a standard inhibition curve are prepared. In this method, the $^{125}$I-radiolabeled MIF antigen competes physiochemically with the non-labeled MIF. After a suitable incubation period, the antigen-antibody complexes, or bound antigen, are separated from the free, unbound antigen and the radioactivity of either or both phases is measured.

In the drawing:

FIG. 1 is a graphical representation or standard curve which shows the inhibition of the reaction between rabbit anti-MIF serum and $^{125}$I-MIF by various amounts of unlabeled MIF antigen.

DETAILED DESCRIPTION OF THE INVENTION

Figure 1:
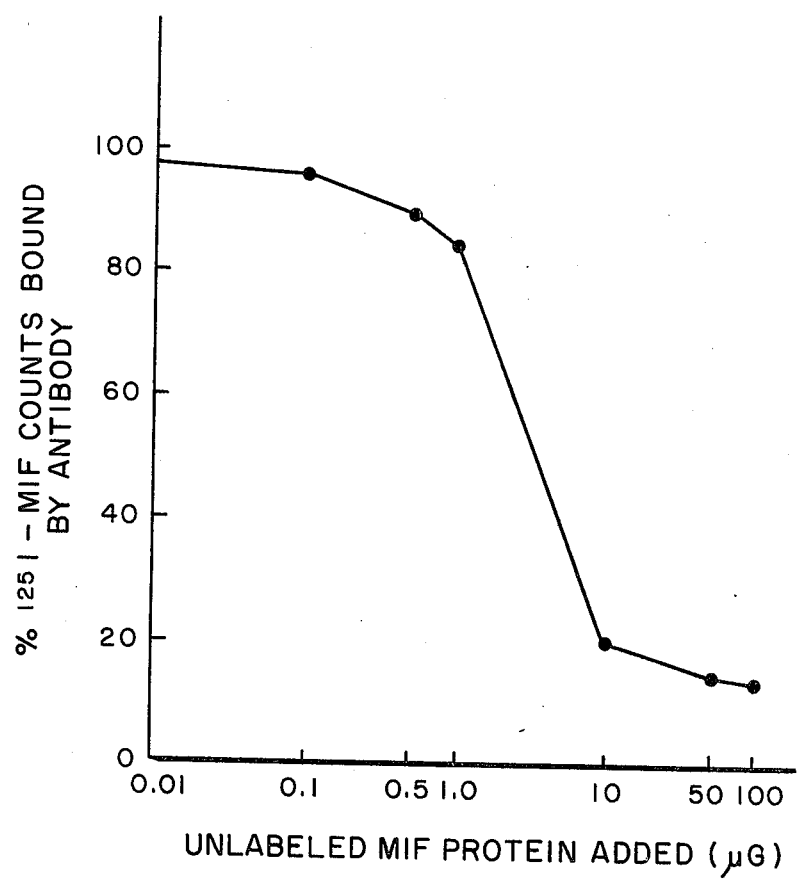

In accordance with the invention, a preferred human cell source of MIF antigen is the transformed lymphocyte cell line PGLC-33H obtained from P. Glade. This is a well characterized and established cell line described by Glade and Papageorgiou, *In Vitro* 9, 202–15 (1973), and Papageorgiou et al., *J. Immunol.* 112, 675–82 (1974).

Other established human lymphoid cell lines which can be used as a source of MIF antigen are well known as disclosed, for example, by Granger et al., *J. Immunol.* 104, 1476–85 (1970) and Papageorgiou et al., *J. Immunol.* 108, 494–504 (1972).

The lymphocyte cells are grown in a serum-free nutrient culture media containing assimilable sources of nitrogen, carbon and inorganic salts at about 37° C. for a suitable culture period, e.g. 24–48 hours. A preferred medium is RPMI-1640 media, available from Grand Island Biological Co., Grand Island, N.Y. (GIBCO), and described by Morton, *In Vitro* 6, 89–108 (1970). The cells are then sedimented by centrifugation, and the cell-free supernatant medium is retained as the active MIF antigen-containing source material.

The MIF antigen-containing cell culture supernatant is then partially purified by dialysis against several large volume (e.g., 4 liters) changes of physiological saline (0.15 N NaCl) followed by sucrose concentration and separation by chromatographic procedures. Use of a hydrophilic, water-insoluble cross-linked dextran polymer gel column is preferred. Sephadex ® G-100 which is commercially available from Pharmacia Fine Chemicals AB, Uppsala, Sweden, is a particularly useful dextran polymer gel for this purpose.

The 25,000 molecular weight fraction from the gel filtration is retained as the active MIF antigen fraction. MIF is glycoprotein in nature with a molecular weight of about 25,000 daltons and migrates with the albumin containing fraction on acrylamide gel electrophoresis at pH 9.1.

In the production of the antibodies against MIF antigen, it has been found to be useful to amplify the antigenicity of the available MIF antigen to stimulate the anti-MIF antibody formation in the host animal. For this purpose, the antigen preferably is bound to a fucosamine-agarose resin which is commercially available from Miles-Yeda, Israel. In affinity chromatography with the fucosamine-agarose resin, the MIF antigen binds to the resin which can be separated from the soluble non-binding proteins by centrifugation. MIF-active protein can be removed from the resin by elution with 0.1 M fucose solution as described by Fox and MacSween, *Immunological Communications* 3, 375–89 (1974).

In the immunization process, the host animal preferably is injected at 2–4 week intervals with antigen in Freund's complete adjuvant as follows: The soluble MIF antigen is injected intradermally and simultaneously MIF bound to the fucosamine-agarose resin is injected via the intraperitoneal route.

The following example will further illustrate the invention although it will be appreciated that the invention is not limited to this specific example or the details recited therein.

EXAMPLE

PGLC-33H cells are cultured in spinner flasks using RPMI-1640 medium (Grand Island Biological Co., Grand Island, N.Y.) which is free from fetal calf serum. The cells are cultured for 24–48 hours at a cell density of about $5 \times 10^6$ cells per milliliter. After the 24–48 hour incubation period, the cells are separated by centrifugation and the cell supernatant is retained as the active MIF antigen-containing material.

The retained supernatant is placed into cellulosic dialysis tubing and dialyzed against 15–20 liters of physiologic saline (0.15 N NaCl) at 4° C. for 24–48 hours. The dialyzed supernatant is concentrated 20 fold in 50% sucrose solution, dialyzed against 0.15 N NaCl and then subjected to various chromatographic and electrophoretic separation procedures in order to further purify the MIF antigen as follows:

A Sephadex ® G-100 column is calibrated with pure protein markers of known molecular weight (albumin—69,000 M.W.; ovalbumin—45,000 M.W; chymotrypsinogen—25,000 M.W.; cytochrome C—12,400 M.W.). The dialyzed, concentrated supernatant was applied to the column and the eluant at the position of the 25,000 M.W. chymotrypsinogen marker was retained as the active MIF antigen fraction. About 3% of the total protein applied to the column was recovered in this fraction.

The active MIF antigen (25,000 M.W. fraction) was subjectd to agarose film electrophoresis before and after $^{125}$I-radiolabeling and compared to a normal human serum electrophoresis reference pattern. A small portion (about 3–4%) of the total active MIF antigen (25,000 M.W. material) migrated electrophoretically like albumin. The isoelectric point of human MIF is in the pH 4.0–5.5 range very close to albumin. The MIF bioactivity was found to be retained in the chromatographically purified fraction after $^{125}$I-radiolabeling.

The MIF in the dialyzed cell supernatant was bound to fucosamine-agarose resin by mixing resin and supernatant (batch method) overnight (about 15 hours) at 4° C. The resin-MIF complex was sedimented by centrifugation and a portion of the MIF was eluted from the resin using a small volume (about 5–10 ml) of 0.1 M fucose while the remainder of the resin-MIF complex was left intact.

Female New Zealand white rabbits (8–10 lbs. each) were immunized every 2–4 weeks with MIF antigen bound to fucosamine-agarose resin intraperitoneally and simultaneously intradermally with soluble unbound MIF antigen (purified as above) emulsified with Freund's complete adjuvant. [See Freund, *Ann. Rev. Microbiol.* 1, 291 (1947) and *Amer. J. Clin. Pathol.* 21, 645 (1951)]. Blood samples were drawn from the rabbits before the immunization protocol began to provide a non-immune serum control sample, and, at regular intervals during the immunization schedule. All rabbit sera were tested for antibody activity against human MIF. After about 70–80 days of immunization, the rabbits developed antibodies in their serum which were able to block MIF activity in cell migration bioassay tests. The pre-immune control sera did not contain anti-MIF antibodies and hence did not block MIF activity.

$^{125}$I-radiolabeling was carried out substantially in accordance with the Chloramine T procedure of Hunter and Greenwood, *Biochem. J.* 91, 46 (1964). The MIF antigen and $^{125}$Iodine isotope were mixed and incubated about 30 seconds in the presence of the oxidizing agent Chloramine-T. During this time $^{125}$I-isotope chemically combines with oxidized hydroxyl groups of the tyrosine residues in the MIF protein. Addition of sodium metabisulfite stops the iodination process. The protein solution contains $^{125}$I-labeled protein and unreacted $^{125}$I-isotope which are then separated from each other by column chromatography on Sephadex ® G-75 resin.

Rabbit anti-MIF serum (1:25 dilution) was added to the $^{125}$I-MIF preparation (10,000 counts per minute). Under these conditions, there is antigen-antibody combination but no immune precipitation occurs. That is, the [antibody. $^{125}$I-MIF] immune complexes are completely soluble due to the antigen ($^{125}$I-MIF) excess relative to the amount of antibody present. Various amounts of unlabeled MIF (0.01 μg-100 μg MIF protein) were added to the system and the assay was incubated at 4° C. for 48 hours. A second serum, goat antiserum against rabbit gamma globulin, was added to the system and incubated at 4° C. for 48 hours in order to precipitate the [rabbit anti-MIF. $^{125}$I-MIF] immune complexes out of solution. Immune precipitates were collected by centrifugation and counted (for $^{125}$I) in a Packard gamma counter. The percent of $^{125}$I counts bound by the antiserum was then calculated for each amount of unlabeled MIF protein standard added and the results were plotted using a semi-log scale.

The entire RIA procedure was also carried out using non-immune rabbit serum in order to determine the amount of non specific binding of $^{125}$I-MIF in the RIA test. The non-specific binding by non-immune serum was insignificant (less than 10%).

The actual MIF-RIA standard curve obtained using the aforesaid system is presented in FIG. 1. It can be seen that addition of as little as 0.1 μg of unlabeled MIF preparation to the system was able to decrease the percentage of $^{125}$I-MIF bound by antibody. There is a linear decline in the percentage of $^{125}$I-MIF bound between one and 10 μg MIF. This shows that the RIA test is sufficiently sensitive to measure as little as one μg MIF protein in a patient sample.

It will be appreciated that variations and modifications of the above-described invention will be apparent to the person skilled in the art after reading of this disclosure without departing from the spirit and scope of the invention. All such variations and modifications are included within the scope of the appended claims.

We claim:

1. A method of detecting the presence of a low level of migration inhibitory factor material in a test solution comprising reacting
   (a) a test solution containing an unknown amount of migration inhibitory factor antigen,
   (b) a known amount of purified migration inhibitory factor antigen which has been radiolabeled,
   (c) a known amount of antibodies having high specificity to migration inhibitory factor,
and thereafter precipitating and separating the resulting antigen-antibody complex from unbound antigen and measuring the radioactive content of said complex, said antibodies to migration inhibitory factor being produced by immunization of animals with purified migration inhibitory factor antigen obtained from the growth of human lymphocytes under tissue culture conditions.

2. The method of claim 1 in which the human lymphocyte cell source of the migration inhibitory factor antigen is the transformed cell line PGLC-33H.

3. The method of claim 1 in which the migration inhibitory factor antigen is purified by affinity chromatography with fucosamine-agarose resin.

4. The method of claim 1 in which a substantial portion of the migration inhibitory factor antigen used in the immunization is bound to fucosamine-agarose resin.

5. The method of claim 1 in which migration inhibitory factor antigen used in the immunization is administered intradermally as unbound migration inhibitory factor antigen simultaneously with intraperitoneal administration of migration inhibitory factor antigen bound to fucosamine-agarose resin.

6. The method of claim 1 in which the migration inhibitory factor antigen used in the immunization is an extract of the growth of human lymphocytes under tissue culture conditions purified by cross-linked dextran gel polymer column chromatography.

7. The method of claim 1 in which the radiolabel is $^{125}$I.

8. The method of claim 1 in which the human lymphocyte cell source of the migration inhibitory factor antigen is the transformed cell line PGLC-33H and in which a substantial portion of the migration inhibitory factor antigen used in the immunization is bound to fucosamine-agarose resin 9. The method of claim 8 in which the migration inhibitory factor antigen used in the immunization is an extract of the growth of the PGLC-33H cells under tissue culture conditions purified by cross-linked dextran gel polymer column chromatography.

10. The method of claim 9 in which migration inhibitory factor antigen used in the immunization is administered intradermally as unbound migration inhibitory factor antigen simultaneously with intrateritoneal administration of migration inhibitory factor antigen bound to fucosamine-agarose resin.

11. The method of claim 10 in which the radiolabel is $^{125}$I.

* * * * *

UNITED STATES PATENT AND TRADEMARK OFFICE
CERTIFICATE OF CORRECTION

PATENT NO. : 4,299,814

DATED : November 10, 1981

INVENTOR(S) : Eva J. Brandt and Samuel S. Asculai

It is certified that error appears in the above—identified patent and that said Letters Patent is hereby corrected as shown below:

IN THE CLAIMS, column 6, line 48,"intrateritoneal" should read --intraperitoneal--.

Signed and Sealed this

Second Day of February 1982

[SEAL]

Attest:

Attesting Officer

GERALD J. MOSSINGHOFF

Commissioner of Patents and Trademarks